(12) United States Patent
Cao et al.

(10) Patent No.: US 12,213,828 B2
(45) Date of Patent: Feb. 4, 2025

(54) IMAGE DATA INSPECTION METHOD AND APPARATUS, COMPUTER DEVICE, AND STORAGE MEDIUM

(71) Applicant: TENCENT TECHNOLOGY (SHENZHEN) COMPANY LIMITED, Shenzhen (CN)

(72) Inventors: Shilei Cao, Shenzhen (CN); Hualuo Liu, Shenzhen (CN); Yefeng Zheng, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 468 days.

(21) Appl. No.: 17/721,806

(22) Filed: Apr. 15, 2022

(65) Prior Publication Data

US 2022/0233160 A1  Jul. 28, 2022

Related U.S. Application Data

(63) Continuation of application No. PCT/CN2021/081206, filed on Mar. 17, 2021.

(30) Foreign Application Priority Data

Apr. 30, 2020 (CN) .......................... 202010367441.0

(51) Int. Cl.
*A61B 6/00* (2024.01)
*A61B 6/03* (2006.01)
(Continued)

(52) U.S. Cl.
CPC ............ *A61B 6/5241* (2013.01); *A61B 6/032* (2013.01); *G06T 7/0012* (2013.01); *G06V 10/16* (2022.01);
(Continued)

(58) Field of Classification Search
CPC ..... A61B 6/032; A61B 6/5241; G06T 7/0012; G06T 2207/10081; G06T 2207/30061;
(Continued)

(56) References Cited

U.S. PATENT DOCUMENTS 10,140,709 B2 * 11/2018 Kisilev ............... A61B 5/7485
2015/0269449 A1   9/2015 Kosaki
(Continued)

FOREIGN PATENT DOCUMENTS

CN        110111313 A      8/2019
CN        110309842 A     10/2019
(Continued)

OTHER PUBLICATIONS

Computer English Translation of Chinese Patent No. CN 110111313 A. (Year: 2019).*
(Continued)

*Primary Examiner* — Daniel G Mariam
(74) *Attorney, Agent, or Firm* — ANOVA LAW GROUP PLLC

(57) ABSTRACT

This application relates to an image data inspection method and apparatus in the field of artificial intelligence (AI) technologies. The method includes obtaining an image to be inspected, the image to be inspected comprising a sequence of slice images; determining a corresponding group of slice images for each target image in the sequence of slice images; extracting a corresponding slice feature map for each slice image in the group of slice images; aligning the slice feature maps extracted corresponding to the group of slice images; aggregating context information of each slice image in the group of slice images by using an aligned feature map; and performing target region inspection on an aggregated feature map, to obtain an inspection result corresponding to the target image, and combining the inspection result corre-
(Continued)

sponding to each target image, to generate an inspection result corresponding to the image to be inspected.

20 Claims, 8 Drawing Sheets

(51) Int. Cl.
    *G06T 7/00*     (2017.01)
    *G06V 10/10*     (2022.01)
    *G06V 10/24*     (2022.01)
    *G06V 10/77*     (2022.01)
    *G06V 10/774*     (2022.01)

(52) U.S. Cl.
    CPC .......... *G06V 10/24* (2022.01); *G06V 10/7715* (2022.01); *G06V 10/774* (2022.01); *G06T 2207/10081* (2013.01); *G06T 2207/30061* (2013.01)

(58) Field of Classification Search
    CPC ...... G06V 10/16; G06V 10/24; G06V 10/774; G06V 10/7715
    See application file for complete search history.

(56) References Cited

U.S. PATENT DOCUMENTS

| | | |
|---|---|---|
| 2017/0262995 A1 | 9/2017 | Li et al. |
| 2020/0034948 A1 | 1/2020 | Park et al. |
| 2021/0264599 A1 | 8/2021 | Gong |

FOREIGN PATENT DOCUMENTS

| | | |
|---|---|---|
| CN | 110633640 A | 12/2019 |
| CN | 110852242 A | 2/2020 |
| CN | 111583220 A | 8/2020 |
| JP | 2015184908 A | 10/2015 |
| WO | 2019005722 A1 | 1/2019 |

OTHER PUBLICATIONS

The European Patent Office (EPO) The Extended European Search Report for 21797835.2 May 9, 2023 15 Pages (including translation).
Yan Ke et al., "3D Context Enhanced Region-Based Convolutional Neural Network for End-to-End Lesion Detection", Sep. 26, 2018 (Sep. 26, 2018), 16th European Conference—Computer Vision-ECCV 2020, Cornell University Library,201Olin Library Cornell University Ithaca, NY14853, pp. 511-519 , XP047557651,[retrieved on Sep. 26, 2018].
Xu Xuanang et al: "Efficient Multiple Organ Localization in CT Image Using 3D Region Proposal Network", IEEE Transactions On Medical Imaging, IEEE, USA, vol. 38, No. 8, Aug. 1, 2019 (Aug. 1, 2019), pp. 1885-1898, XP011736957,ISSN: 0278-0062, DOI:10. 1109/TMI.2019.2894854[retrieved on Jul. 30, 2019].
Hongfeng You et al: "A New Multiple Max-pooling Integration Module and Cross Multiscale Deconvolution Network Based on Image Semantic Segmentation",Arxiv.org, Cornell University Library, 201Olin Library Cornell University Ithaca, NY14853,Mar. 25, 2020 (Mar. 25, 2020), XP081629243.
Ye Chengqin et al: "Multi-Depth Fusion Network for Whole-Heart CT Image Segmentation", IEEE Access, vol. 7, Feb. 15, 2019 (Feb. 15, 2019), pp. 23421-23429, XP011713260,DOI: 10.1109/ACCESS. 2019.2899635 [retrieved on Mar. 4, 2019].
The Japan Patent Office (JPO) Notification of Reasons for Refusal for Application No. 2022-535820 and Translation Apr. 18, 2023 7 Pages.
F. Bray et al., "Global cancer statistics 2018: GLOBOCAN estimates of incidence and mortality worldwide for 36 cancers in 185 countries," CA: A Cancer Journal for Clinicians, vol. 68, No. 6, pp. 394-424, 2018. 31 pages.

V. A. Moyer, "Screening for lung cancer: US preventive services task force recommendation statement," Annals of Internal Medicine, vol. 160, No. 5, 2014, Retrieved from the Internet: URL: https://www.acpjournals.org/doi/full/10.7326/M13-2771, [retrieved on Apr. 7, 2022]. 33 pages.
G. Litjens et al., "A survey on deep learning in medical image analysis," arXiv:1702.05747v2, Jun. 4, 2017. 38 pages.
J. Ding et al., "Accurate pulmonary nodule detection in computed tomography images using deep convolutional neural networks," arXiv:1706.04303v3, Aug. 29, 2017. 9 pages.
Q. Dou et al., "Automated pulmonary nodule detection via 3D ConvNets with online sample filtering and hybrid-loss residual learning," arXiv:1708.03867v1, Aug. 13, 2017. 3 pages.
R. H. Abiyev et al., "Deep convolutional neural networks for chest diseases detection," Journal of Healthcare Engineering, vol. 2018, Article ID 4168538, 2018. 11 pages.
T.-Y. Lin et al., "Feature pyramid networks for object detection," arXiv:1612.03144V2, Apr. 19, 2017. 10 pages.
J. Deng et al., "ImageNet: A large-scale hierarchical image database," in Proc. IEEE Conf. Computer Vision and Pattern Recognition. IEEE, 2009. 3 pages.
N. Khosravan et al., "SAND: Single-shot single-scale lung nodule detection," arXiv:1805.02279v2, Jun. 3, 2018. 3 pages.
Z. Tian et al., "FCOS: Fully convolutional one-stage object detection," arXiv preprint arXiv:1904.01355v5, Aug. 20. 2019. 13 pages.
H. Law et al., "CornerNet: Detecting objects as paired keypoints," arXiv:1808.01244v2, Mar. 18, 2019. 14 pages.
K. Duan et al., "CenterNet: Object detection with keypoint triplets," arXiv preprint arXiv:1904.08189v1, Apr. 17, 2019. 10 pages.
S. Ren et al., "Faster R-CNN: Towards Real-Time Object Detection with Region Proposal Networks," arXiv:1506.01497v3, Jan. 6, 2016. 14 pages.
F. Liao et al., "Evaluate the Malignancy of Pulmonary Nodules Using the 3D Deep Leaky Noisy-or Network," arXiv:1711. 08324v1, Nov. 22, 2017. 12 pages.
K. Yan et al., "Deep lesion graphs in the wild: Relationship learning and organization of significant radiology image findings in a diverse large-scale lesion database," arXiv:1711.10535v3, Jul. 28, 2018. 16 pages.
K. Yan et al., "3D context enhanced regionbased convolutional neural network for end-to-end lesion detection," arXiv:1806. 09648v2, Jul. 29, 2018. 11 pages.
M. Muhler et al., "The influence of slice thickness on assessment of clavicle ossification in forensic age diagnostics," International Journal of Legal Medicine, vol. 120, No. 1, pp. 15-17, 2006. 3 pages.
F. Fischbach et al., "Detection of pulmonary nodules by multislice computed tomography: Improved detection rate with reduced slice thickness," European Radiology, vol. 13, No. 10, pp. 2378-2383, 2003. 6 pages.
M. J. Murphy , "The importance of computed tomography slice thickness in radiographic patient positioning for radiosurgery," Medical Physics, vol. 26, No. 2, pp. 171-175, 1999. 5 pages.
W. G. Bradley et al., "The effect of variation in slice thickness and interslice gap on MR lesion detection," American Journal of Neuroradiology, vol. 8, No. 6, pp. 1057-1062, 1987. 6 pages.
J. W. Chadwick et al., "The effects of slice thickness and interslice interval on reconstructed cone beam computed tomographic images," Oral Surgery, Oral Medicine, Oral Pathology, Oral Radiology, and Endodontology, vol. 110, No. 4, pp. e37-e42, 2010. 6 pages.
R. Prabhakar et al., "Impact of different CT slice thickness on clinical target vol. for 3D conformal radiation therapy," Medical Dosimetry, vol. 34, No. 1, pp. 36-41, 2009. 6 pages.
N. J. Schneiders et al., "CT quality assurance: computer assisted slice thickness determination," Medical Physics, vol. 7, No. 1, pp. 61-63, 1980. 3 pages.
J. Redmon et al., "You only look once: Unified, real-time object detection," arXiv:1506.02640v5, May 9, 2016. 10 pages.
T.-Y. Lin et al., "Focal loss for dense object detection," arXiv:1708. 02002v2, Feb. 7, 2018. 10 pages.
A. A. A. Setio et al., "Validation, comparison, and combination of algorithms for automatic detection of pulmonary nodules in computed tomography images: the LUNA16 challenge," arXiv:1612. 08012v4, Jul. 15, 2017. 17 pages.

(56) References Cited

OTHER PUBLICATIONS

K. He et al., "Deep residual learning for image recognition," arXiv:1512.03385v1, Dec. 10, 2015. 12 pages.
Q. Tao et al., "Improving deep lesion detection using 3D contextual and spatial attention," arXiv:1907.04052v1, Jul. 9, 2019. 10 pages.
M. Zlocha et al., "Improving RetinaNet for CT lesion detection with dense masks from weak RECIST labels," arXiv:1906.02283v1, Jun. 5, 2019. 10 pages.
P. O. Pinheiro et al., "Learning to segment object candidates," in Advances in Neural Information Processing Systems, 2015. 9 pages.
K. He et al., "Rethinking ImageNet pre-training," arXiv:1811.08883v1, Nov. 21, 2018. 10 pages.
M. Raghu et al., "Transfusion: Understanding transfer learning for medical imaging," arXiv:1902.07208v3, Oct. 29, 2019. 22 pages.
Y. Wu et al., "Group normalization," arXiv:1803.08494v3, Jun. 11, 2018. 10 pages.
S. Ioffe et al., "Batch normalization: Accelerating deep network training by reducing internal covariate shift," arXiv preprint arXiv:1502.03167v3, Mar. 2, 2015. 11 pages.
X. Wang et al. "Non-local neural networks," Proceedings of the IEEE conference on computer vision and pattern recognition, 2018: 7794-7803. 10 pages.
A. Vaswani et al., "Attention is all you need," in Advances in Neural Information Processing Systems, 2017. 11 pages.
W. Liu et al., "SSD: Single shot multibox detector," arXiv:1512.02325v5, Dec. 29, 2016. 17 pages.
J. Redmon et al., "YOLOv3: An incremental improvement," arXiv preprint arXiv:1804.02767v1, Apr. 8, 2018. 6 pages.
J. Yu et al., "UnitBox: An advanced object detection network," arXiv:1608.01471v1, Aug. 4, 2016. 5 pages.
A. Paszke et al., "PyTorch: An imperative style, high-performance deep learning library," arXiv:1912.01703v1, Dec. 3, 2019. 12 pages.
Z. Cai et al., "Cascade R-CNN: Delving into high quality object detection," arXiv:1712.00726v1, Dec. 3, 2017. 9 pages.
R. Girshick, "Fast R-CNN," arXiv:1504.08083v2, Sep. 27, 2015. 9 pages.
J. Redmon et al., "YOLO9000: Better, faster, stronger," arXiv:1612.0824v1, Dec. 25, 2016. 9 pages.
K. Chen et al., "MMDetection: Open MMLab detection toolbox and benchmark," arXiv preprint arXiv:1906.07155v1, Jun. 17, 2019. 13 pages.
Z. Tian et al., "Fcos: Fully Convolutional One-Stage Object Detection," IEEE/CVF International Conference on Computer Vision (ICCV), 2019, pp. 9627-9636. 10 pages.
The World Intellectual Property Organization (WIPO) International Search Report for PCT/CN2021/081206 May 27, 2021 5 Pages (including translation).

* cited by examiner

IMAGE DATA INSPECTION METHOD AND APPARATUS, COMPUTER DEVICE, AND STORAGE MEDIUM

RELATED APPLICATIONS

This application is a continuation application PCT Application No. PCT/CN2021/081206, filed on Mar. 17, 2021, which in turn claims priority to Chinese Patent Application No. 2020103674410, entitled "IMAGE DATA INSPECTION METHOD AND APPARATUS" filed on Apr. 30, 2020. The two applications are incorporated by reference in their entirety.

FIELD OF THE TECHNOLOGY

This application relates to the field of artificial intelligence technologies, and in particular, to an image data inspection method and apparatus, a computer device, a storage medium, and a method and an apparatus for training an image inspection model.

BACKGROUND OF THE APPLICATION

With the research and progress of the AI technology, the AI technology is studied and applied in a plurality of fields, such as a smart home, and an intelligent medical treatment. Using intelligent medical care as an example, detection efficiency can be improved by analyzing medical images through computer programs.

Due to different types of medical appliances, different physical parameters, different scanning protocols, and the like, resolution of image data differs greatly, and target regions differ greatly. Such differences are also referred to as information asymmetry. In a conventional method, resampling is usually used to resolve the problem of information asymmetry, but the computing speed is relatively low. Therefore, how to effectively improve detection efficiency of image data has become a technical problem that needs to be resolved.

SUMMARY

According to various embodiments provided in this application, an image data inspection method and apparatus, a computer device, a storage medium, and a method and an apparatus for training an image inspection model are provided.

One aspect of this disclosure provides an image data inspection method performed by a computer device. The method includes obtaining an image to be inspected, the image to be inspected comprising a sequence of slice images; determining a corresponding group of slice images for each target image in the sequence of slice images, the group of slice images comprising the target image and an adjacent image having a context relationship with the target image in the sequence of slice images; extracting a corresponding slice feature map for each slice image in the group of slice images; aligning the slice feature maps extracted corresponding to the group of slice images; aggregating context information of each slice image in the group of slice images by using an aligned feature map; and performing target region inspection on an aggregated feature map, to obtain an inspection result corresponding to the target image, and combining the inspection result corresponding to each target image, to generate an inspection result corresponding to the image to be inspected.

One or more non-transitory storage mediums storing computer-readable instructions are provided, the computer-readable instructions, when executed by one or more processors, causing the one or more processors to perform the step in the image data inspection method described above.

Another aspect of this disclosure provides a method for training an image inspection model, the image inspection model including a backbone network, a three-dimensional alignment network, a three-dimensional aggregation network, and a target detection network. The method includes determining a corresponding group of slice sample images for each target sample image in a sequence of slice sample images of an image sample; the group of slice sample images comprising the target sample image and an adjacent sample image having a context relationship with the target sample image in the sequence of slice sample images; extracting a corresponding slice sample feature map for each slice sample image in the group of slice sample images through the backbone network; aligning the slice sample feature maps extracted corresponding to the group of slice sample images through the three-dimensional alignment network; aggregating context information of each slice sample image in the group of slice sample images through the three-dimensional aggregation network by using an aligned sample feature map; and performing target region inspection on an aggregated sample feature map through the target detection network, to obtain an inspection result corresponding to the target sample image, and combining the inspection result corresponding to each target sample image, to generate an inspection result corresponding to the image sample.

A computer device is provided, including a memory and a processor, the memory storing computer-readable instructions, and the computer-readable instructions, when executed by the processor, causing the processor to perform: obtaining an image to be inspected, the image to be inspected comprising a sequence of slice images; determining a corresponding group of slice images for each target image in the sequence of slice images, the group of slice images comprising the target image and an adjacent image having a context relationship with the target image in the sequence of slice images; extracting a corresponding slice feature map for each slice image in the group of slice images; aligning the slice feature maps extracted corresponding to the group of slice images; aggregating context information of each slice image in the group of slice images by using an aligned feature map; and performing target region inspection on an aggregated feature map, to obtain an inspection result corresponding to the target image, and combining the inspection result corresponding to each target image, to generate an inspection result corresponding to the image to be inspected.

One or more non-transitory storage mediums storing computer-readable instructions are provided, the computer-readable instructions, when executed by one or more processors, causing the one or more processors to perform the steps in the method for training an image inspection model described above.

Details of one or more embodiments of this application are provided in the subsequent accompanying drawings and descriptions. Other features, objectives, and advantages of this application are illustrated in the specification, the accompanying drawings, and the claims.

BRIEF DESCRIPTION OF THE DRAWINGS

To describe the technical solutions in embodiments of this application more clearly, the following briefly describes the accompanying drawings required for describing the embodiments. Apparently, the accompanying drawings in the following description show merely some embodiments of this application, and a person of ordinary skill in the art may still derive other accompanying drawings from these accompanying drawings without creative efforts.

DESCRIPTION OF EMBODIMENTS

To make the objectives, technical solutions, and advantages of this application clearer and more understandable, this application is further described in detail below with reference to the accompanying drawings and the embodiments. It is to be understood that the specific embodiments described herein are only used for explaining this application, and are not used for limiting this application.

Figure 1:
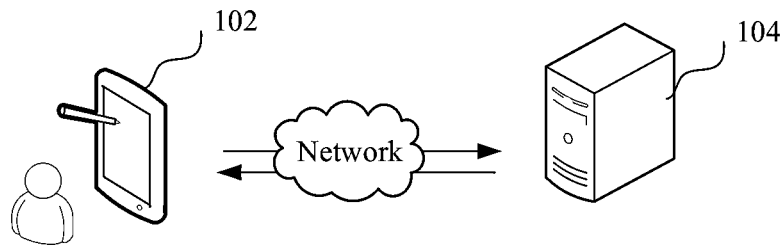
FIG. 1 is an application environment diagram of an image data inspection method according to an embodiment.

An image data inspection method provided in this application may be applied to an application environment shown in FIG. 1. A terminal 102 communicates with a server 104 through a network. The terminal 102 may be, but is not limited to, various personal computers, notebook computers, smartphones, tablet computers, and portable wearable devices. The server 104 may be an independent physical server, or may be a server cluster including a plurality of physical servers or a distributed system, or may be implemented by a cloud server that provides basic cloud computing services such as a cloud database, cloud storage, cloud communication, and big data and artificial intelligence (AI) platforms. The terminal 102 obtains an image to be inspected, generates a detection task by using the image to be inspected, and uploads the detection task to the server 104. The server 104 invokes an image inspection model to perform the detection task. The server 104 obtains a group of slice images corresponding to each target image from a sequence of slice images of the image to be inspected. The group of slice images includes the target image and an adjacent image having a context relationship with the target image in the sequence of slice images. The server 104 extracts a corresponding slice feature map for each slice image in the group of slice images through an image inspection model, and performs an alignment operation on the slice feature maps extracted corresponding to the group of slice images. Context information of the each slice image in the group of slice images is aggregated by using an aligned feature map, target region inspection is performed on an aggregated feature map, to obtain an inspection result corresponding to the target image, and the inspection result corresponding to the each target image is combined, to generate an inspection result corresponding to the image to be inspected. The server 104 returns the inspection result to the terminal 102.

Figure 2:
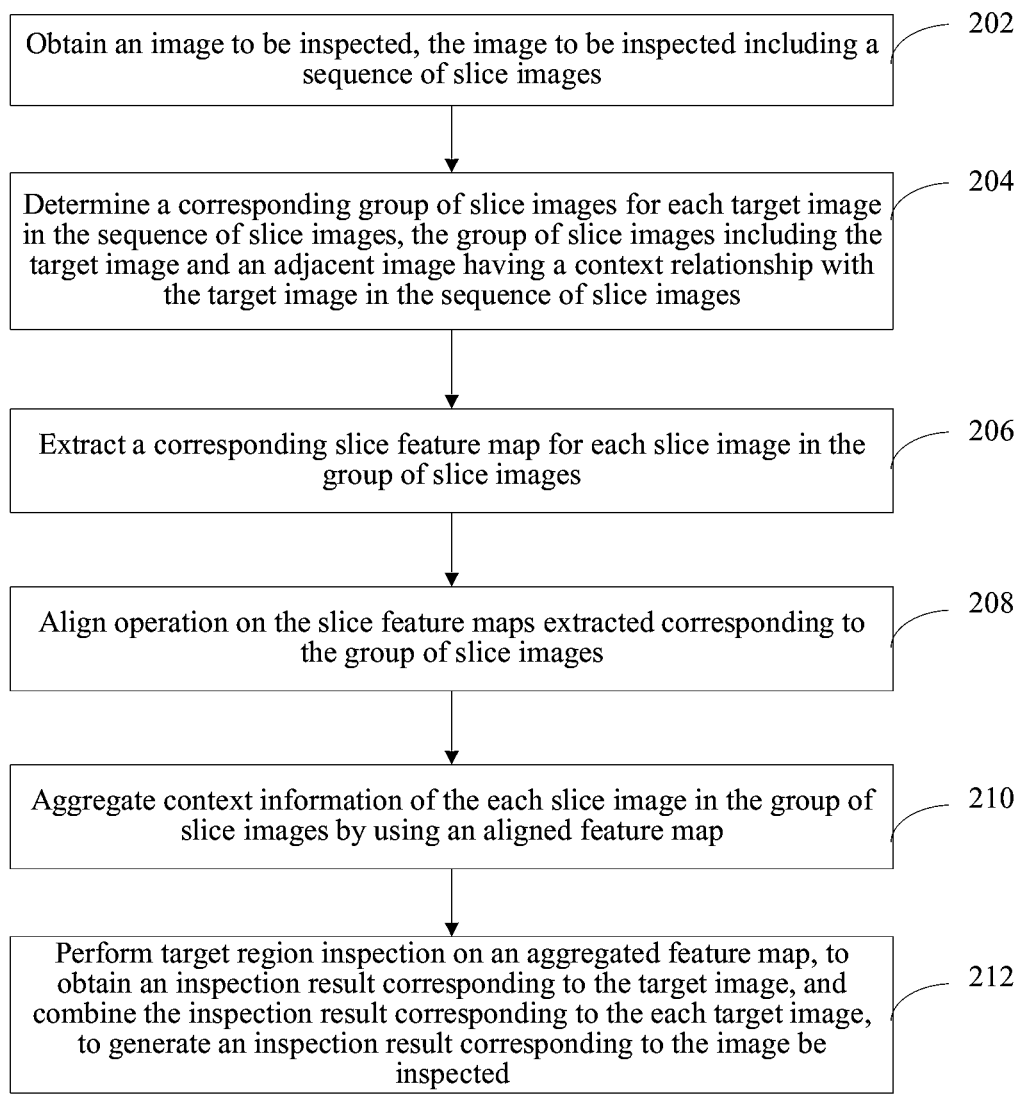
FIG. 2 is a schematic flowchart of an image data inspection method according to an embodiment.

In an embodiment, as shown in FIG. 2, an image data inspection method is provided. That the method is applied to the server in FIG. 1 is used as an example for description. It can be understood that the method may also be applied to a terminal. In this embodiment, the following steps are included:

Step 202. Obtain an image to be inspected, the image to be inspected including a sequence of slice images.

The server may obtain a detection task in a manner provided in the foregoing application scenario, and obtain the image to be inspected according to the detection task. The image to be inspected may be a captured medical image of a part to be detected or the like, for example, a captured CT image of a lung. The image to be inspected is a three-dimensional image, with information in a horizontal direction and a depth direction. The horizontal direction may be represented by a direction x and a direction y. The depth direction may be represented by a direction z. In each direction, there is a corresponding distance between pixels. The distance may be referred to as an interval of a corresponding direction. The horizontal direction can reflect plane information in a slice image. The depth direction can reflect space information between slice images. The image to be inspected includes the sequence of slice images. The sequence of slice images includes a plurality of slice images. A plurality of slice images means three or more slice images. The slice image is a two-dimensional image. The slice image reflects a current status of the part to be detected.

Step 204. Determine a corresponding group of slice images for each target image in the sequence of slice images, the group of slice images including the target image and an adjacent image having a context relationship with the target image in the sequence of slice images.

Figure 3:
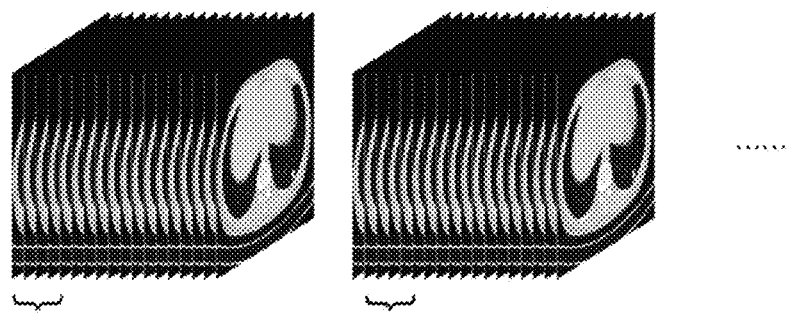
FIG. 3 is a schematic diagram of obtaining a slice image through a sliding window according to an embodiment.

The server sequentially obtains a preset quantity of adjacent slice images along the depth direction through a sliding window from the sequence of slice images, as a group of slice images to be detected, as shown in FIG. 3. The sliding window is a fixed-size window that can be slid by a fixed step. The fixed step may be determined according to a distance between two adjacent slice images. The sliding window obtains the same quantity of slice images each time. After obtaining a group of slice images to be detected, the sliding window may be slid by a fixed step, to obtain a next group of slice images to be detected. A previous group of slice images to be detected includes the same quantity of images as a next group of slice images to be detected. A next group of slice images to be detected includes all slice images except the first slice image in the previous group of slice images to be detected. The preset quantity may be an odd number. For example, the preset quantity is T, and T=2M+1, where the first M slice images and the last M slice images constitute context of the middle slice image. The middle slice image may be referred to as a target image. A group of slice images to be detected corresponding to the target image may be referred to as a group of slice images. In an embodiment, after obtaining a group of slice images to be detected, the sliding window may alternatively be slid by a random step to obtain a next group of slice images to be detected. The random step may alternatively be determined according to a distance between two adjacent slice image. For example, the random step may be a random multiple of a distance between two adjacent slice images.

Step 206. Extract a corresponding slice feature map for each slice image in the group of slice images.

In this embodiment, the detection task may be performed through a pre-trained image inspection model. The image inspection model includes a two-dimensional backbone network, a three-dimensional alignment network, a three-dimensional aggregation network, and a target detection network. The two-dimensional backbone network is used for extracting a feature of a slice image. The two-dimensional backbone network includes a ResNet (residual neural network) and a feature pyramid network (FPN, a multi-scale target detection algorithm). The ResNet in this embodiment has fewer input channels in the first convolutional layer than the original ResNet, and has the fully connected layer at the end deleted. The channel input in the first convolutional layer is changed from original three channels to one channel. Because the slice image is a grayscale image, the slice image can be directly used as an input of the ResNet by reducing the channels of the first convolutional layer. Because the fully connected layer is generally used for classifying a task, in this embodiment, the ResNet is not required for classification. Therefore, after the fully connected layer at the end of the original ResNet is deleted, the ResNet may be combined with the FPN to form a two-dimensional backbone network. All convolutions in the two-dimensional backbone network are two-dimensional convolutions.

The server sequentially inputs each slice image in the group of slice images into the two-dimensional backbone network for feature extraction, and obtains the slice feature map corresponding to each slice image. For example, if the quantity of the slice images in the group of slice images is T, T independent slice feature maps may be obtained. A size of the slice feature map may be determined according to a quantity of channels of the two-dimensional backbone network, a preset width, and a preset height. For example, the size of the slice feature map is (C, W, H), where C, W, and H respectively represent the quantity of channels of the two-dimensional backbone network, a slice preset width, and a slice preset height. Because the slice images are individually output to the two-dimensional backbone network, no information exchange occurs between the slice images, allowing three-dimensional structure information of a photographed part to be preserved. In addition, two-dimensional convolutions are used in the two-dimensional backbone network for feature extraction of the slice images, so that a computation amount can be effectively reduced, thereby improving image detection efficiency.

Step 208. Align operation on the slice feature maps extracted corresponding to the group of slice images.

The server inputs the slice feature maps extracted corresponding to the group of slice images into the three-dimensional alignment network, stitches the slice feature maps extracted corresponding to the group of slice images through the three-dimensional alignment network, and determines a size of a stitched feature map according to a size of each slice feature map and a quantity of the slice feature maps. For example, if the size of the slice feature map is (C, W, H), and the quantity of the slice feature maps extracted corresponding to the group of slice images is T, the size of the stitched feature map is (C, T, W, H).

C, W, and H in the slice feature map may respectively represent a channel dimension, a slice width dimension, and a slice height dimension, which may also be referred to as existing dimensions. In the stitched feature map, T may represent a slice quantity dimension. For the stitched feature map, the three-dimensional alignment network learns internal information of the slice image based on the existing dimensions, and learns the space information between the slice images based on the slice quantity dimension. Normalization is performed in the existing dimensions and the slice quantity dimension, to output the aligned feature map. The size of the aligned feature map is the same as that of the stitched feature map. The slice width dimension and the slice height dimension may also be collectively referred to as a slice size dimension, or a slice plane dimension. The slice quantity dimension may also be referred to as a slice space dimension.

In the conventional method, during detection of slice images, alignment is performed only in the slice plane dimension, and alignment in the slice space dimension is not considered, lacking information exchange on the three-dimensional structure, and causing a problem of information asymmetry between slice images. In this embodiment, the alignment operation is performed on the stitched feature map in the slice plane dimension and the slice space dimension through the three-dimensional alignment network, thereby adjusting information between different slice images to the same distribution space. This can effectively resolve the problem of large resolution differences between slice images and information asymmetry between the slice images, thereby effectively improving image accuracy.

Step 210. Aggregate context information of each slice image in the group of slice images by using an aligned feature map.

The aligned feature map is input into the three-dimensional aggregation network. The three-dimensional aggregation network reshapes the aligned feature map according to the slice quantity dimension and the existing dimensions (that is, the channel dimension, the slice width dimension, and the slice height dimension), to generate at least two reshaped feature maps. An arrangement manner of slice quantity dimension information may vary in different reshaped feature maps. The reshaped feature maps are weighted by using the slice quantity dimension, and dimensionality reduction is performed on the weighted feature maps, to generate the aggregated feature map corresponding to the group of slice images.

The three-dimensional aggregation network utilizes a self-attention mechanism that directs the attention of the image inspection model to important regions and ignores unimportant regions. Through feature aggregation of the slice feature map of each slice image in the group of slice images, information that is more discriminative is extracted from slice images having a context relationship, and the information that is more discriminative is fused together. After the three-dimensional aggregation network, a feature map fused with context information can be directly output.

Step 212. Perform target region inspection on an aggregated feature map, to obtain an inspection result corresponding to the target image, and combine the inspection result corresponding to the each target image, to generate an inspection result corresponding to the image to be inspected.

An anchor-free detector may be used for the target detection network. The target detection network includes a plurality of branches, including a classification branch, a regression branch, and a center point prediction branch. The target detection network identifies whether each pixel in the aggregated feature map falls within a target detection box. The classification branch identifies a category corresponding to a pixel falling within the target detection box. The regression branch performs regression to obtain a plurality of sides, for example, four sides, of the pixel falling within the target detection box, to form one bounding box. The center point prediction branch predicts a relative distance between the pixel and a center point of the target detection box. A longer distance indicates a lower confidence level. When the relative distance exceeds a preset distance, the bounding box of the sample pixel is filtered out. The target detection network detects each pixel in the aggregated feature map, to obtain an inspection result of the target image in the group of slice images.

After completing feature extraction on the current group of slice images, the server inputs the next group of slice images obtained through the sliding window into the two-dimensional backbone network. The sliding window obtains the same quantity of slice images each time. There is a difference of one slice image between a next sliding window and a previous sliding window in the depth direction. A slice image in the next group of slice images is detected in the foregoing manner, to obtain an inspection result of a target image in the next group of slice images. The inspection result corresponding to each target image is combined, to generate an inspection result corresponding to the image to be inspected.

Figure 4:
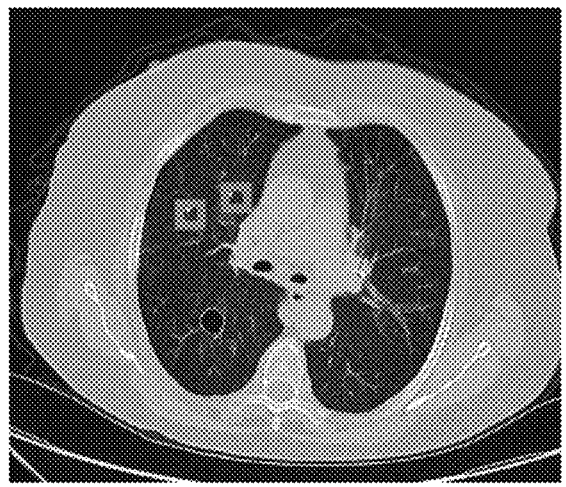
FIG. 4 is a schematic diagram of a lung image inspection result of a conventional three-dimensional convolutional neural network according to an embodiment.
Figure 5:
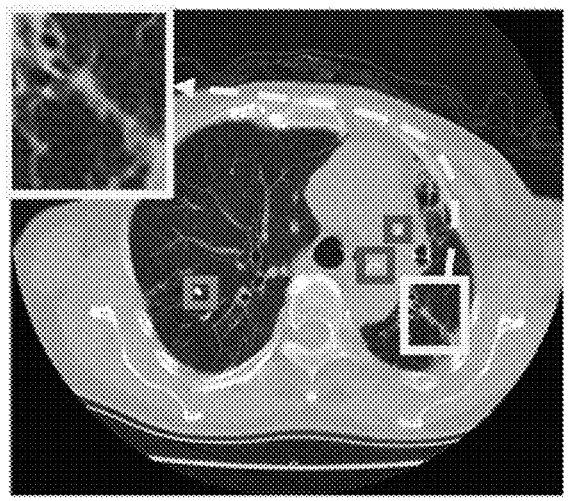
FIG. 5 is a schematic diagram of a lung image inspection result of an image inspection model according to an embodiment.

In a conventional three-dimensional convolutional neural network detection algorithm, only a specific target region can be detected, and features of other regions are ignored. In the manner provided in this embodiment, not only a specific target region can be detected, but other regions can also be detected. Using a lung CT image as an example, the conventional three-dimensional convolutional neural network can detect only pulmonary nodules, and an inspection result is shown in FIG. 4. In addition to detecting lung modules, the image inspection model in this embodiment can also accurately detect lung cords, arteriosclerosis, lymph node calcification, and the like, as shown in FIG. 5.

In this embodiment, the slice feature map of the each slice image in the group of slice images can be extracted by determining the group of slice images corresponding to the each target image in the sequence of slice images of the image to be inspected. Because feature extraction is individually performed on the slice images, no information exchange occurs between the slice images, allowing three-dimensional structure information of a photographed part to be preserved. Information between different slice images can be adjusted to the same distribution space by performing the alignment operation on the slice feature maps extracted corresponding to the group of slice images, making it possible to apply to an image to be inspected with different orientation intervals in each direction, resolving the problem of image data differences caused by different types of instruments, different physical parameters, different scanning protocols, and the like, effectively suppressing the adverse effects of information asymmetry in each dimension of the image to be inspected, and improving detection accuracy of the image to be inspected. Because there is a context relationship between the target image and the adjacent image in the group of slice images, aggregation of the context information of the each slice image in the group of slice images by using the feature map after the alignment operation can extract features that are more discriminative. Target region inspection is performed on the aggregated feature map, so that an inspection result corresponding to the target image can be obtained, and the inspection result corresponding to the each target image is combined, to generate an inspection result corresponding to the image to be inspected. This not only resolves the problem of information asymmetry of the image to be inspected, but also effectively improves image data detection efficiency.

In an embodiment, the stitching the slice feature maps extracted corresponding to the group of slice images includes: obtaining a slice quantity corresponding to the group of slice images; stacking the slice feature maps extracted corresponding to the group of slice images, a stacked feature map including a slice quantity dimension and a channel dimension; and exchanging a feature of the slice quantity dimension with a feature of the channel dimension, to generate the stitched feature map.

The slice feature map includes features of a plurality of dimensions, such as the channel dimension, the slice width dimension, and the slice height dimension. The dimensions are in a preset order. The server stacks the slice feature maps extracted corresponding to the group of slice images, and determines a size of a stacked feature map according to a size of each slice feature map and a quantity of the slice feature maps. The stacked feature map additionally has a slice quantity dimension on the basis of the original dimensions. After the stacking of the slice feature maps, the order of the dimensions changes accordingly. The slice quantity dimension may rank before the existing dimensions, or may rank after the existing dimensions, or may be interspersed with the existing dimensions. For example, the order of the dimensions may change to the slice quantity dimension, the channel dimension, the slice width dimension, and the slice height dimension. In order to resolve the problem of information asymmetry between the slice images, the feature of the slice quantity dimension may be exchanged with the feature of the channel dimension.

For example, the size of the slice feature map is (C, W, H), where C, W, and H respectively represent the channel dimension, the slice width dimension, and the slice height dimension. The slice quantity corresponding to the group of slice images is T, the T slice feature maps are stacked, and then the slice quantity dimension is added. In this case, a size of a stacked feature map may be expressed as (T, C, W, H). Dimension information of the slice quantity dimension and that of the channel dimension are exchanged to obtain a stitched feature map with a size of (C, T, W, H).

In an embodiment, the performing the alignment operation on a stitched feature map includes performing a three-dimensional convolution operation on the stitched feature map; normalizing the slice quantity dimension and the slice size dimension of the feature map after the convolution operation; and outputting the aligned feature map by performing nonlinear activation on the normalized feature map.

The slice feature maps extracted corresponding to the group of slice images are stitched, to generate the stitched feature map. The server inputs the stitched feature map into a three-dimensional alignment network. The three-dimensional alignment network includes a three-dimensional convolutional layer, a group normalization layer, and a nonlinear activation layer. The three-dimensional convolutional layer in the three-dimensional alignment network includes at least one three-dimensional convolution, and a convolution operation is performed on the stitched feature map through the three-dimensional convolutional layer. In order to effectively reduce model parameters and a computational amount, a convolution kernel of the three-dimensional convolution may be a convolution kernel of a relatively small size, for example, a convolution kernel of (3, 1, 1), for performing the convolution operation on the stitched feature map. Through the convolution operation, the stitched feature map is smoothed, internal information of the slice image is learned in the existing dimensions (the channel dimension, the slice width dimension, and the slice height dimension), and space information between the slice images is learned in the slice quantity dimension. The three-dimensional convolutional layer may learn the internal information of the slice image in the slice width dimension and the slice height dimension. In the conventional method, the three-dimensional convolutional layer learns only the internal information of the slice image through the convolution operation, and lacks learning of space information, thus lacking information exchange on the three-dimensional structure. In this embodiment, different slice feature maps are aligned, so that the problem of information asymmetry caused by large differences in features in each direction within and between slices can be effectively alleviated.

In the conventional method, normalization is performed in the group normalization layer only in the slice width dimension and the slice height dimension. In this embodiment, normalization is performed in the group normalization layer not only in the slice width dimension and the slice height dimension but also in the slice quantity dimension. Accordingly, the adverse effects of slice features in the horizontal direction and the depth direction are eliminated.

The normalized feature map is processed by the nonlinear activation layer. The nonlinear activation layer may use an activation function, for example, a ReLU function, to output the aligned feature map. The size of the aligned feature map may be the same as that of the stitched feature map. For example, the size of the stitched feature map is (C, T, W, H), and the size of the feature map may also be (C, T, W, H).

In this embodiment, the slice images extracted corresponding to the group of slice images are stitched, and the alignment operation is performed by using the stitched feature map, thus making it possible to apply to an image to be inspected with different orientation intervals in the plane direction and the depth direction, resolving the problem of image data differences caused by different types of instruments, different physical parameters, different scanning protocols, and the like, effectively suppressing the adverse effects of information asymmetry in each dimension of the image to be inspected, and effectively improving detection accuracy of the image to be inspected.

In an embodiment, the aggregating context information of the each slice image in the group of slice images by using an aligned feature map includes: reshaping the aligned feature map according to a slice quantity dimension, to generate a reshaped feature map; and weighting the aligned feature map by using the reshaped feature map, and performing dimensionality reduction on the weighted feature map, to generate an aggregated feature map corresponding to the group of slice images.

The slice images in the group of slice images include the target image and an adjacent image having a context relationship with the target image. For example, the preset quantity is T, and T=2M+1, where the first M slice images before the middle slice image and the last M slice images after the middle slice image constitute the group of slice images. The first M slice images and the last M slice images constitute context of the middle slice image.

The three-dimensional aggregation network reshapes the aligned feature map according to the slice quantity dimension and the existing dimensions (the channel dimension, the slice width dimension, and the slice height dimension), to generate at least two reshaped feature maps. Dimension information of the existing dimensions is combined and then resorted with slice quantity dimension information, for reshaping. For example, the size of the aligned feature map may also be (C, T, W, H), reshaped into (T, C*W*H) and (C*W*H, T).

In one embodiment, the three-dimensional aggregation network transforms the reshaped feature map, and weights the slice quantity dimension of the aligned feature map by using the transformed feature map; and obtains a dimensionality reduction convolution, and performs dimensionality reduction on the weighted feature map by using the dimensionality reduction convolution.

Point multiplication is performed on the reshaped feature map, to obtain a matrix of two rows and two columns corresponding to the slice quantity dimension. Accordingly, the reshaped feature map is transformed. For example, point multiplication is performed on (T, C*W*H) and (C*W*H, T), to obtain a matrix of (T, T). After going through an activation function Sigmoid, the matrix and the slice quantity dimension in the aligned feature map are multiplied. The aligned feature map is weighted by weighting an added dimension, to obtain the weighted feature map. A size of the weighted feature map is the same as that of the aligned feature map. For example, the size of the aligned feature map is (C, T, W, H), and the size of the weighted feature map is also (C, T, W, H).

The convolution operation is performed on the weighted feature map by using the dimensionality reduction convolution to perform dimensionality reduction on the weighted feature map. The dimensionality reduction convolution may be a three-dimensional convolution, and a convolution kernel thereof may be generated according to a slice quantity corresponding to the group of slice images. For example, the convolution kernel of the dimensionality reduction convolution is (T, 1, 1). Through dimensionality reduction, a weighted feature map with a size of (C, T, W, H) is changed into a feature map with a size of (C, W, H). The feature map may be referred to as an aggregated feature map. This is equivalent to aggregating the context information into the feature map of the target image.

In a weighted processing method of the related technology, all pixels in an image to be inspected are weighted, and no dimensionality reduction is involved for a weighted feature map. In this embodiment, the overall aligned feature map of each slice image in the group of slice images is weighted. In addition, dimensionality reduction is performed on the weighted feature map by using the three-dimensional dimensionality reduction convolution, so that a three-dimensional feature map is dimensionality reduced to a two-dimensional feature map, effectively reducing a computation amount, thereby effectively improving detection efficiency.

In this embodiment, through aggregation of the context information of each slice image in the group of slice images, information that is more discriminative is extracted from context slice images, and the information that is more discriminative is fused together. After the three-dimensional aggregation network, a feature map fused with context information can be directly output, so that a more accurate inspection result of the image to be inspected can be obtained.

In a specific embodiment, an image data inspection method is provided, specifically including:
    obtaining an image to be inspected, the image to be inspected including a sequence of slice images; determining a corresponding group of slice images for each target image in the sequence of slice images, the group of slice images including the target image and an adjacent image having a context relationship with the target image in the sequence of slice images; extracting a corresponding slice feature map for each slice image in the group of slice images; obtaining a slice quantity corresponding to the group of slice images; stacking the slice feature maps extracted corresponding to the group of slice images, a stacked feature map including a slice quantity dimension and a channel dimension; and exchanging a feature of the slice quantity dimension with a feature of the channel dimension, to generate a stitched feature map; performing a three-dimensional convolution operation on the stitched feature map; normalizing the slice quantity dimension and the slice size dimension of the feature map after the convolution operation; and outputting an aligned feature map by performing nonlinear activation on the normalized feature map; reshaping the aligned feature map according to a slice quantity dimension, to generate a reshaped feature map; transforming the reshaped feature map, and weighting the slice quantity dimension of the aligned feature map by using the transformed feature map; obtaining a dimensionality reduction convolution, and performing dimensionality reduction on the weighted feature map by using the dimensionality reduction convolution, to generate an aggregated feature map corresponding to the group of slice images; identifying a category corresponding to a pixel falling within a target detection box in the aggregated feature map; performing regression to obtain a bounding box of the pixel, and predicting a relative distance between the pixel and a center point of the target detection box; and filtering out the bounding box of the pixel when the relative distance exceeds a preset distance, to obtain an inspection result corresponding to the target image, and combining the inspection result corresponding to the each target image, to generate an inspection result corresponding to the image to be inspected.

Figure 6:
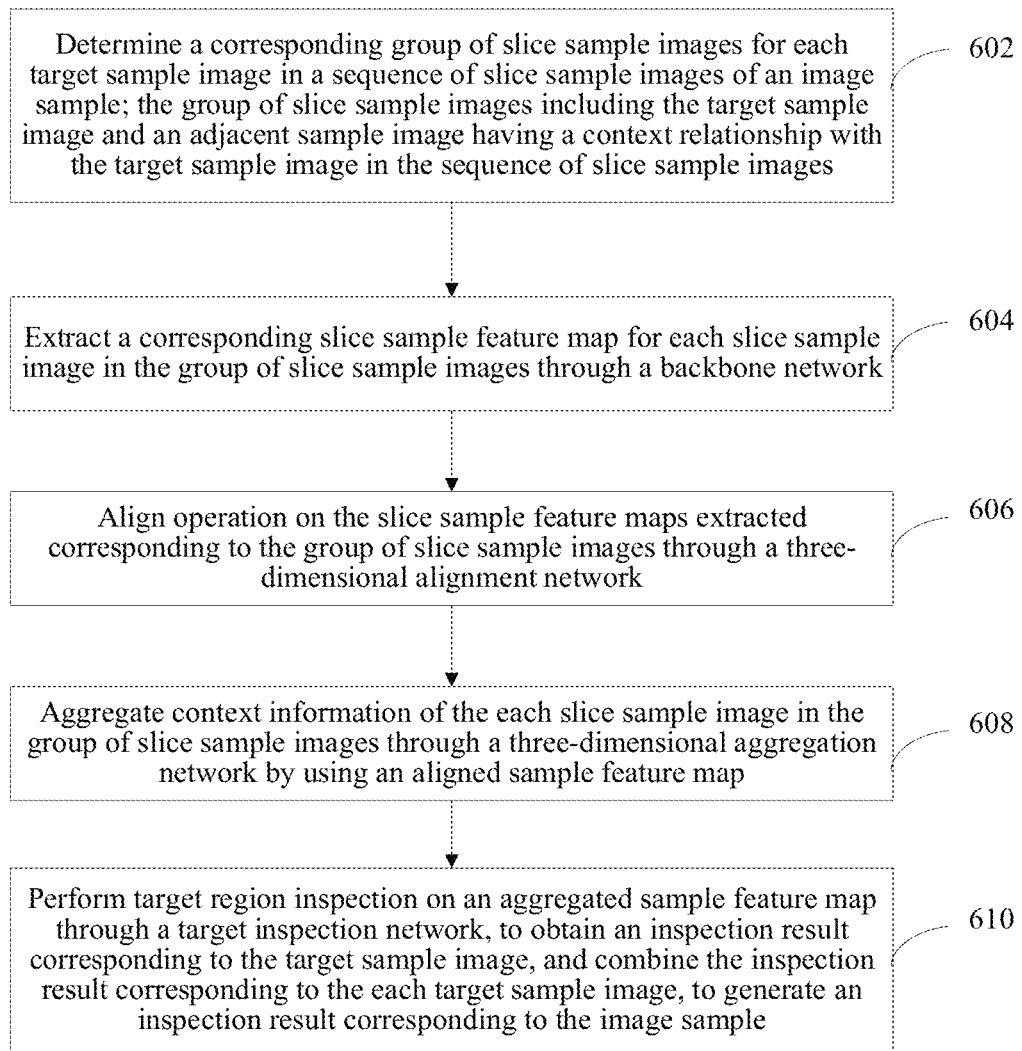
FIG. 6 is a schematic flowchart of a method for training an image inspection model according to an embodiment.

In an embodiment, as shown in FIG. 6, a method for training an image inspection model is provided. The image inspection model includes a backbone network, a three-dimensional alignment network, a three-dimensional aggregation network, and a target detection network. The method for training includes the following steps:

Step 602. Determine a corresponding group of slice sample images for each target sample image in a sequence of slice sample images of an image sample; the group of slice sample images including the target sample image and an adjacent sample image having a context relationship with the target sample image in the sequence of slice sample images.

Step 604. Extract a corresponding slice sample feature map for each slice sample image in the group of slice sample images through the backbone network.

Step 606. Align operation on the slice sample feature maps extracted corresponding to the group of slice sample images through the three-dimensional alignment network.

Step 608. Aggregate context information of each slice sample image in the group of slice sample images through the three-dimensional aggregation network by using an aligned sample feature map.

Step 610. Perform target region inspection on an aggregated sample feature map through the target detection network, to obtain an inspection result corresponding to the target sample image, and combine the inspection result corresponding to the each target sample image, to generate an inspection result corresponding to the image sample.

Figure 7:
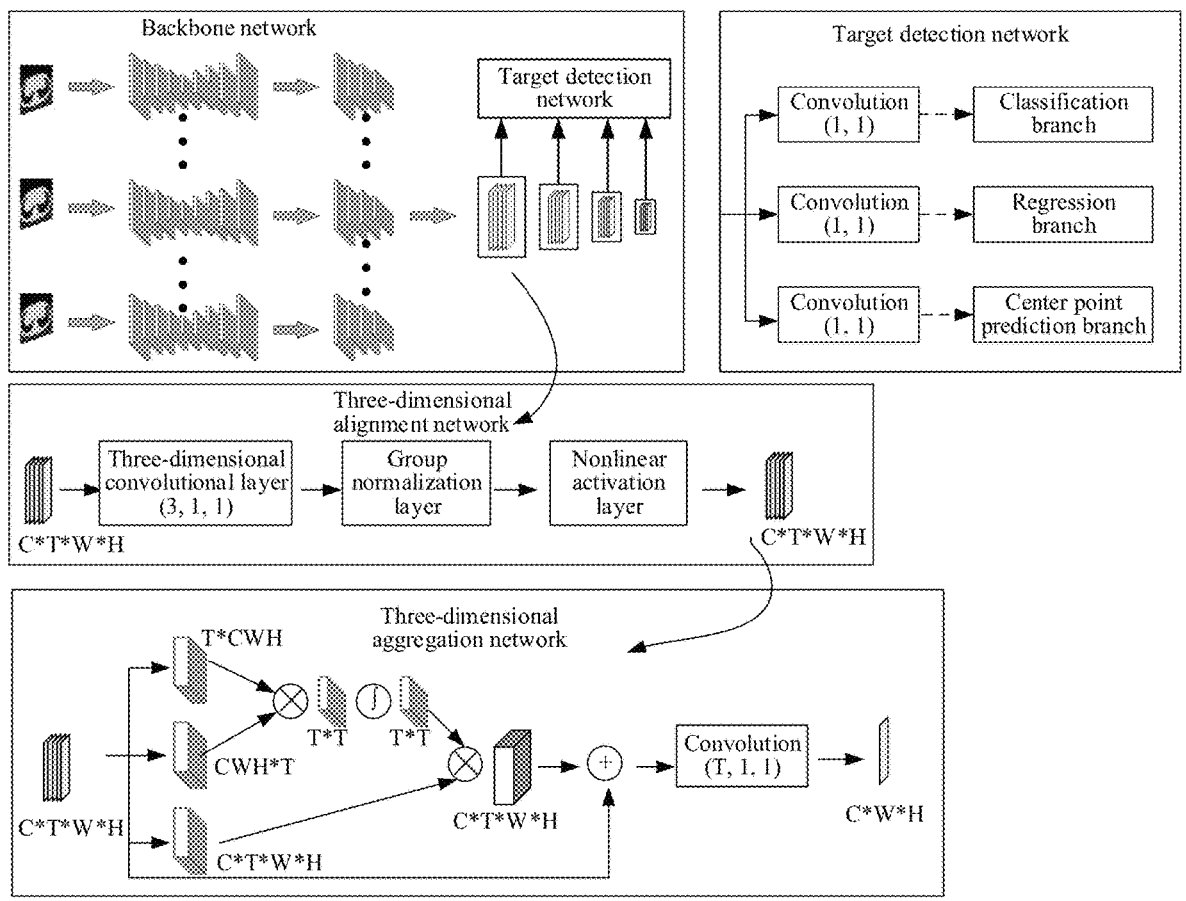
FIG. 7 is a schematic diagram of a network structure of an image inspection model according to an embodiment.

A training data set includes various types of image samples. The image sample includes a plurality of slice samples. Various types of detection targets are labeled in the slice sample. Because a magnitude of an image value has a physical meaning, image values of different magnitudes correspond to different detection parts. A fixed size may be set for each detection part, and a size of a corresponding slice sample is cropped to the fixed size. For example, a slice sample of a CT image for lung detection is cropped to [−1200, 600]. The cropped slice sample is standardized, and the standardized slice sample is used as an input of a model, to fit a mean and a variance input by a training model. A computer device trains the image inspection model by using the standardized slice sample. The image inspection model includes a two-dimensional backbone network, a three-dimensional alignment network, a three-dimensional aggregation network, and a target detection network. A network structure of the image inspection model is shown in FIG. 7.

Standardized slice samples corresponding to the image samples are sorted in a depth direction, to form a sequence of slice sample images of the image samples. The computer device obtains, by using a sliding window, a preset quantity of slice samples along the depth direction as a group of training samples. The group of training samples may also be referred to as a group of slice sample images. The group of slice sample images includes the target sample image and an adjacent sample image having a context relationship with the target sample image in the sequence of slice sample images. For example, the quantity of the slice samples in the group of slice sample images is T, and T=2M+1, where the first M slice sample images and the last M slice sample images constitute context of the middle slice sample image. The middle slice sample image may be referred to as a target sample image. Each slice sample image in the group of slice sample images is input into the two-dimensional backbone network, to extract a slice sample feature map corresponding to each slice sample image. The slice sample images extracted corresponding to the group of slice sample images are stitched through the three-dimensional alignment network, and an alignment operation is performed by using a stitched sample feature map, to generate the aligned sample feature map. Context information of each slice sample image in the group of slice sample images through the three-dimensional aggregation network by using the aligned sample feature map, to obtain an aggregated sample feature map.

An aggregated training feature map is input into the target detection network. The target detection network includes a plurality of branches, including a classification branch, a regression branch, and a center point prediction branch. Each branch includes several convolutional layers, a batch norm layer, and a ReLU layer. The target detection network individually processes each pixel in the aggregated training feature map. For each pixel in the aggregated training feature map, if the pixel falls within a target detection box, it is considered as a positive sample; otherwise, it is considered as a negative sample. For each positive sample, the classification branch classifies a region represented by the pixel. The regression branch performs regression to obtain a plurality of sides, for example, four sides, of the pixel falling within the target detection box, to form one complete bounding box. For pixels falling within a plurality of target detection boxes, a detection box with a smallest area is selected as a regression target. The center point prediction branch predicts a relative distance between the pixel distance and a center point of the target detection box. A longer relative distance indicates a lower confidence level. When the relative distance exceeds a preset distance, the bounding box of the pixel is filtered out. Accordingly, an error bounding box far away from a target center region can be filtered out. For example, an error bounding box far away from a disease center region can be filtered out.

In this embodiment, the slice sample feature map of each slice sample image in the group of slice sample images can be extracted by determining the group of slice sample images corresponding to the each target sample image in the sequence of slice sample images of the image sample. Because feature extraction is individually performed on the slice sample images, no information exchange occurs between the slice sample images, allowing three-dimensional structure information of a photographed part to be preserved. Information between different slice sample images can be adjusted to the same distribution space by performing the alignment operation on the slice sample feature maps extracted corresponding to the group of slice sample images, making it possible to apply to an image sample with different orientation intervals in each direction, resolving the problem of image data differences caused by different types of instruments, different physical parameters, different scanning protocols, and the like, effectively suppressing the adverse effects of information asymmetry in each dimension of the image sample, and improving detection accuracy of the image sample. Because there is a context relationship between the target sample image and the adjacent image in the group of slice sample images, aggregation of the context information of each slice sample image in the group of slice sample images by using the sample feature map after the alignment operation can extract features that are more discriminative. Performing target region inspection on an aggregated sample feature map can obtain an inspection result corresponding to the target sample image, and the inspection result corresponding to each target sample image is combined, to generate an inspection result corresponding to the image sample. This not only resolves the problem of information asymmetry of the image sample, but also effectively improves detection efficiency of the image sample.

In an embodiment, the performing an alignment operation on the slice sample feature maps extracted corresponding to the group of slice sample images through the three-dimensional alignment network includes: stitching the slice sample images extracted corresponding to the group of slice sample images through the three-dimensional alignment network, and performing the alignment operation by using a stitched sample feature map, to generate the aligned sample feature map.

The computer device obtains a slice sample quantity corresponding to the group of slice sample images. The slice sample quantity is the quantity of the slice sample feature maps. The computer device stacks the slice sample feature maps extracted corresponding to the group of slice sample images, and determines a size of a stacked sample feature map according to a size of each slice sample feature map and the quantity of the slice sample feature maps. The stacked sample feature map additionally has a slice quantity dimension on the basis of the original dimensions. In order to resolve the problem of information asymmetry between the slice images, the feature of the slice quantity dimension may be exchanged with the feature of the channel dimension, to generate the stitched sample feature map. The three-dimensional alignment network includes a three-dimensional convolutional layer, a group normalization layer, and a nonlinear activation layer. A three-dimensional convolution operation is performed on the stitched sample feature map through the three-dimensional convolutional layer. The slice quantity dimension and the slice size dimension of the sample feature map after the convolution operation is normalized through the group normalization layer. Nonlinear activation is performed on the normalized sample feature map through the nonlinear activation layer, to output the aligned sample feature map.

In the conventional method, the three-dimensional convolutional layer learns only the internal information of the slice image through the convolution operation, and lacks learning of space information, thus lacking information exchange on the three-dimensional structure. In this embodiment, different slice sample feature maps are aligned, so that the problem of information asymmetry caused by large differences in features in each direction within and between slice samples can be effectively alleviated. In the conventional method, normalization is performed in the group normalization layer only in the slice width dimension and the slice height dimension. In this embodiment, normalization is performed in the group normalization layer not only in the slice width dimension and the slice height dimension but also in the slice quantity dimension. Accordingly, the adverse effects of slice sample features in the horizontal direction and the depth direction are eliminated.

In an embodiment, the aggregating context information of the each slice sample image in the group of slice sample images through the three-dimensional aggregation network by using an aligned sample feature map includes: reshaping the aligned sample feature map according to a slice quantity dimension through the three-dimensional aggregation network, to generate a reshaped sample feature map; and weighting the aligned sample feature map by using the reshaped sample feature map, and performing dimensionality reduction on the weighted sample feature map, to generate an aggregated sample feature map corresponding to the group of slice sample images.

The three-dimensional aggregation network reshapes the aligned sample feature map according to the slice quantity dimension and the existing dimensions (the channel dimension, the slice width dimension, and the slice height dimension), to generate at least two reshaped sample feature maps. The three-dimensional aggregation network performs point multiplication on the reshaped sample feature map, to obtain a matrix of two rows and two columns corresponding to the slice quantity dimension. Accordingly, the reshaped sample feature map is transformed. After going through an activation function Sigmoid, the matrix and the slice quantity dimension in the aligned sample feature map are multiplied. The aligned sample feature map is weighted by weighting the slice quantity dimension, to obtain the weighted sample feature map. Dimensionality reduction is performed on the weighted sample feature map by using a dimensionality reduction convolution, to generate an aggregated sample feature map. For example, the size of the aligned sample feature map may be (C, T, W, H), reshaped into (T, C*W*H) and (C*W*H, T). Point multiplication is performed on (T, C*W*H) and (C*W*H, T), to obtain a matrix of (T, T). After going through the activation function Sigmoid and the weighting, a weighted sample feature map with a size of (C, T, W, H) is obtained. A convolution kernel of the dimensionality reduction convolution is (T, 1, 1). Through dimensionality reduction, a weighted sample feature map with a size of (C, T, W, H) is changed into an aggregated sample feature map with a size of (C, W, H).

In this embodiment, the three-dimensional aggregation network utilizes a self-attention mechanism that directs the attention of the model to important regions and ignores unimportant regions. Through aggregation of the context information of each slice sample image in the group of slice sample images, information that is more discriminative is extracted from context slice sample images, and the information that is more discriminative is fused together. After the three-dimensional aggregation network, a sample feature map fused with context information can be directly output, so that a more accurate inspection result can be obtained.

In an embodiment, the target detection network includes a classification branch, a regression branch, and a center point prediction branch. The performing target region inspection on an aggregated sample feature map through the target detection network includes: identifying a category corresponding to a sample pixel falling within a target detection box in the aggregated sample feature map through the classification branch; performing regression through the regression branch to obtain a bounding box of the sample pixel; and predicting a relative distance between the sample pixel and a center point of the target detection box through the center point prediction branch, and filtering out the bounding box of the sample pixel when the relative distance exceeds a preset distance.

In this embodiment, an anchor-free detector is used for the target detection network. The target detection network includes a classification branch, a regression branch, and a center point prediction branch. The target detection network has a corresponding loss function. The loss function includes a plurality of loss sub-functions, including a loss function including a classification loss function corresponding to the classification branch, a regression loss function corresponding to the regression branch, and a center point prediction loss function corresponding to the center point prediction branch. The final loss function Loss is defined as follows:

Loss=Classification Loss+Offset Loss+Center-ness Loss where Classification Loss is the classification loss function, Offset Loss is the regression loss function, and Centerness Loss is the center point prediction loss function.

The target detection network is mapped to an original input slice sample image (briefly referred to as an input image) for each pixel in the sample feature map fused with context information. A position of each pixel may be represented as (x, y). Coordinates mapped to the input image may be (xs+s/2, ys+s/2), where s is a scaling coefficient of a current level to the input image. If a pixel mapped back to the input image falls within the target detection box, it is considered as a positive sample; otherwise, it is considered as a negative sample. For each positive sample, the classification branch classifies a category represented by the pixel. For example, the category may be a disease category. The regression branch performs regression to obtain a plurality of sides, for example, four sides, of the pixel falling within the target detection box, to form one complete bounding box, that is, a target position. For example, the target position is a disease position. For pixels falling within a plurality of target detection boxes, a detection box with a smallest area is selected as a regression target. For each positive sample, regression may be performed to obtain a corresponding target of (l, t, r, b), that is, distances from a center point of the bounding box to sides on the top, bottom, left, and right. $(x_0, y_0)$ and $(x_1, y_1)$ respectively represent coordinate values of the upper-left and lower-right corners of the bounding box. A formula for regression training is shown in the following formula (1).

$$l=x-x_0^{(i)}, t=y-y_0^{(i)}$$

$$r=x_1^{(i)}-x, b=y_1^{(i)}-y \qquad (1)$$

The center point prediction branch is parallel to the classification branch, which is equivalent to adding a loss to the network. The loss ensures that the predicted bounding box is as close as possible to the center point of the target detection box. A formula for the center point prediction loss function is shown in formula (2).

$$\text{Centerness Loss} = \sqrt{\frac{\min(l, r)}{\max(l, r)} \times \frac{\min(t, b)}{\max(t, b)}} \qquad (2)$$

The center point prediction loss function can predict a plurality of distances related to the center point of the target detection box, for example, distances from the center point of the target detection box to the upper-left and lower-right four sides of the target region. Therefore, the center point of the target detection box and the four distances can directly determine a rectangular box. The center point prediction branch predicts a relative distance between the pixel distance and the center point of the target detection box. A longer relative distance indicates a lower confidence level. When the relative distance exceeds a preset distance, the bounding box of the pixel is filtered out. Accordingly, an error bounding box far away from a target center region can be filtered out. For example, an error bounding box far away from a disease center region can be filtered out.

For example, the target detection box may be a lesion region, and the center point of the target detection box may be a lesion center. When a pixel falls within a target detection box, it belongs to a positive sample, and the classification branch classifies a disease category thereof. Regression is performed through the regression branch to obtain the bounding box of the pixel. If a distance between the pixel and the lesion center is at a preset distance, it is predicted to be positive for a particular type of disease in combination with its corresponding classification. If the distance to the lesion center point exceeds the preset distance, it is predicted to be false positive for a particular type of disease in combination with its corresponding classification. Accordingly, an error bounding box far away from a lesion center region can be filtered out, thereby effectively improving detection accuracy.

Training of the image inspection model can enable the image inspection model to learn general features, and the image inspection model is further trained after a training set is fine-tuned. This can effectively reduce model overfitting, accelerate a model convergence effect, and improve accuracy and efficiency of image detection.

In an embodiment, during training, the computer device obtains a slice thickness, and determines an adjustment quantity according to the slice thickness; and performs a non-maximum suppression operation by using the adjustment quantity of slice sample images, to remove redundant detection boxes.

A inspection result of each slice sample image is obtained through detection after a plurality of adjacent slice images are obtained through the sliding window. When a plurality of sliding windows contain the intersection of slice sample images, it is necessary to use non-maximum suppression (NMS) to select windows with the highest scores (highest target probability) in the neighborhood and suppress windows with low scores. In order to effectively improve accuracy of the inspection result, the NMS may be adaptively adjusted according to the slice thickness. Specifically, a slice quantity used for adjusting the NMS may be determined according to the slice thickness, and the quantity may also be referred to as a slice adjustment quantity. The slice quantity may be represented by N, and N=C/S, where C is a constant, and S is the slice thickness. The constant may be determined according to an empirical value during training, for example, 30. A cross-slice NMS operation is performed by using N slice images, to suppress redundant detection boxes. Accordingly, target detection efficiency can be effectively improved.

That the image sample is a lung CT image is used as an example to compare and describe other detection methods of training results of the image inspection model of this application.

The training set includes 1470 lung CT images, with 12218 annotations in total, including four thoracic diseases: pulmonary nodules (PN, 3264 cases), lung cords (FS, 3613 cases), arteriosclerosis (TAA, 4201 cases), and lymph node calcification (LNC, 1140 cases). In the lung CT images in the training set, spacings between pixels within a slice sample differ greatly and slice sample thicknesses differ greatly (such differences are referred to as information asymmetry). A spacing between pixels within a slice sample ranges from 0.46 mm to 0.98 mm, and a slice sample thickness ranges from 1.0 mm to 14.8 mm. 1176 CT images are randomly selected from the training set for training, and the remaining 294 CT images are tested. The slice samples of the CT images are each 512×512 pixels, and the slice samples may be randomly flipped horizontally for data augmentation.

The problem of information asymmetry cannot be well resolved through the conventional resampling operation. Experiments were conducted by using the currently popular two-dimensional first-order detector RetinaNet and three-dimensional detector 3D RPN. Resolutions of four experiments were respectively: an original resolution and resampling resolutions of 0.7 mm×0.7 mm×0.7 mm, 1 mm×1 mm×1 mm, and 0.7 mm×0.7 mm×5 mm. Results of the four experimental setups are shown in Table 1. A FROC average score can reflect a false positive rate of model detection. A higher FROC score indicates higher accuracy of detection and a lower false positive rate. It can be seen from Table 1 that resampling does not improve performance of the two-dimensional RetinaNet, and resampling at different resolutions causes essential differences to results of the two-dimensional RetinaNet, but resampling at different resolutions has little impact on results of the three-dimensional RPN. It can be learned that the resampling operations cannot effectively resolve the problem of information asymmetry.

TABLE 1

| Resolution after resampling | FROC average score | |
| --- | --- | --- |
| | RetinaNet | 3D RPN |
| Without resampling (original resolution) | 0.389 | 0.307 |
| 0.7 mm × 0.7 mm × 0.7 mm | 0.216 | 0.323 |

TABLE 1-continued

| Resolution after resampling | FROC average score | |
| --- | --- | --- |
| | RetinaNet | 3D RPN |
| 1 mm × 1 mm × 1 mm | 0.237 | 0.302 |
| 0.7 mm × 0.7 mm × 5 mm | 0.358 | 0.315 |

It can be seen from the FROC average score in Table 1 that the best result of the 2D RetinaNet is better than that of the 3D RPN. This indicates that a two-dimensional network is more suitable for resolving the problem of information asymmetry than a three-dimensional network.

The image inspection model in this application is a hybrid network combining a two-dimensional network and a three-dimensional network. The backbone network is a two-dimensional network. The three-dimensional alignment network, the three-dimensional aggregation network, and the target detection network are each a three-dimensional network. The backbone network includes the ResNet and the FPN. Both the internal information of the slice image and the information between the slice images are critical for image detection. Because the internal information of the slice image is easily processed by a two-dimensional neural network, a natural idea is to simulate a three-channel image and fuse the information between the slice images in the first convolutional layer of the network. Contrary to this idea, the image inspection model proposed in this application fuses the information between the slice images after features are extracted through the backbone network. The two fusion methods can be compared experimentally.

Different quantities of adjacent slices in the first convolutional layer are fused to examine the effectiveness of classical RetinaNet in utilizing context information. The results in rows (a), (b), and (c) in Table 2 do not show a corresponding improvement as the quantity of context slice images increases. This indicates that the RetinaNet cannot exploit context information directly through the context information and a single convolutional layer. Using the fusion method in this application, the results are shown in rows (d) and (e) in Table 2. The same quantity of slice images are input, and an improvement of 0.023 is obtained in terms of the FROC average score in the row (d). According to a result of comparison between the rows (e) and (d) in Table 2, the three-dimensional alignment network achieves an improvement of 0.007 in terms of the FROC average score. Comparing the rows (f) and (g), the three-dimensional aggregation network brings an improvement of 0.008 to the FROC average score. For differences in slice thicknesses, non-maximal predictions of nearby slices are suppressed by additional cross-slice NMS. Comparing the rows (g) and (h), it shows that the FROC average score is increased by 0.011. In contrast to the anchor-based detection method of RetinaNet, the target detection network of this application is an anchor-free detector. The result shown in the row (d) of Table 2, compared with that in the row (c) of Table 2, has an improvement of 0.015. In Table 2, 2M+1 is a quantity of slice sample images in the group of slice sample images. AFH, SAI, 3DRAM, 3DFM, and CS-NMS are respectively an anchor detection head, an anchor-free detection head, a two-dimensional backbone network, a three-dimensional alignment network, a three-dimensional aggregation network, and cross-slice NMS. PN, FS, TAA, and LNC respectively represent pulmonary nodules, lung cords, arteriosclerosis, and lymph node calcification.

TABLE 2

| 2M + 1 | Method | AFH | SAI | 3DRAM | 3DFM | CS-NMS | FROC score | | | | Average score |
|---|---|---|---|---|---|---|---|---|---|---|---|
| | | | | | | | PN | FS | TAA | LNC | |
| 1 | (a) RetinaNet | | | | | | 0.309 | 0.221 | 0.447 | 0.566 | 0.386 |
| 3 | (b) RetinaNet | | | | | | 0.361 | 0.217 | 0.428 | 0.551 | 0.389 |
| 5 | (c) RetinaNet | | | | | | 0.355 | 0.216 | 0.425 | 0.521 | 0.379 |
| 5 | (d) AFH | ✓ | | | | | 0.364 | 0.224 | 0.449 | 0.541 | 0.394 |
| | (e) AFH + SAI | ✓ | ✓ | | | | 0.356 | 0.256 | 0.480 | 0.576 | 0.417 |
| | (f) AFH + SAI + 3DRAM | ✓ | ✓ | ✓ | | | 0.384 | 0.241 | 0.534 | 0.536 | 0.424 |
| | (g) AFH + SAI + 3DRAM + 3DFM | ✓ | ✓ | ✓ | ✓ | | 0.392 | 0.250 | 0.505 | 0.581 | 0.432 |
| | (h) AFH + SAI + 3DRAM + 3DFM + CS-NMS | ✓ | ✓ | ✓ | ✓ | ✓ | 0.395 | 0.262 | 0.530 | 0.584 | 0.443 |

To further examine the advantages of the anchor-free detector in terms of speed and accuracy, the effect of the entire model framework of this application is compared with that of the anchor-free detector and that of the anchor-based detector. Results are as shown in Table 4. The anchor-free detector not only brings an improvement of 0.02 in terms of the FROC average score, but also runs faster than the anchor-based detector in advancing speed per inference.

TABLE 3

| FROC score | PN | FS | TAA | LNC | Average score | Running time |
|---|---|---|---|---|---|---|
| Anchor-based detector | 0.403 | 0.223 | 0.497 | 0.571 | 0.423 | 195 ms |
| Anchor-free detector | 0.395 | 0.262 | 0.530 | 0.584 | 0.443 | 158 ms |

Figure 8:
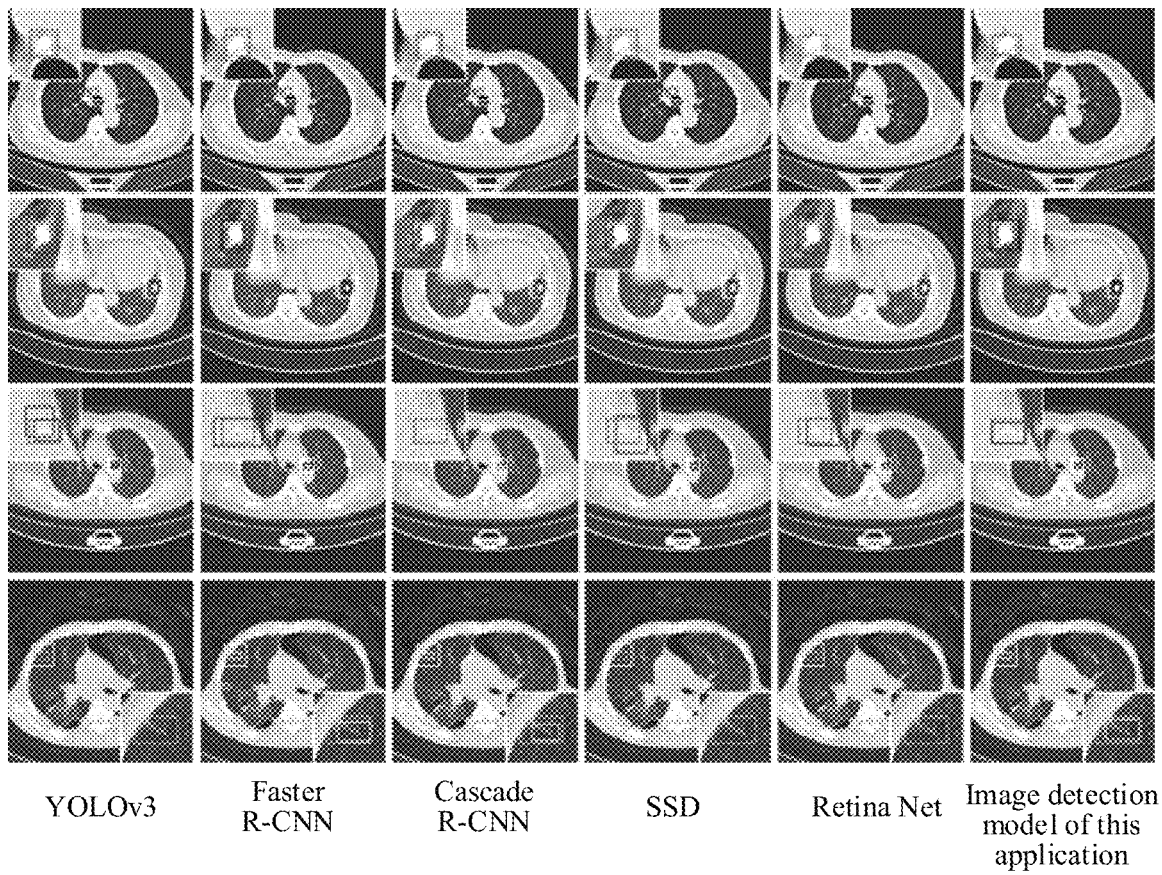
FIG. 8 is a schematic diagram of an inspection result of comparison between an anchor-free detector and an anchor-based detector according to an embodiment.

In the related art, the most advanced anchor-based detectors, including Faster R-CNN, cascade R-CNN, RetinaNet, SSD, YOLOv3, and the like, all rely on pre-defined anchor boxes. In contrast, this application uses the anchor-free detector, which completely avoids complex calculation related to anchor boxes. Comparing the anchor-free detector provided in this application with the foregoing several anchor-based detectors, inspection results are shown in FIG. 8, and specific data comparison results are shown in Table 4. It can be seen from Table 4 that the anchor-free detector provided in this application outperforms other anchor-based detectors by a significant margin. The anchor-based detectors generate more parameters in the network as stages increase, making the models prone to overfitting. In contrast, the image inspection model provided in this application ignores the impact of large changes in data on performance, and therefore, has a strong capability to detect thoracic diseases in datasets with a wide range of resolution settings, achieving a low false positive rate and a low false negative rate.

TABLE 4

| FROC score | PN | FS | TAA | LNC | Average score |
|---|---|---|---|---|---|
| Faster R-CNN | 0.221 | 0.190 | 0.381 | 0.449 | 0.310 |
| Cascade R-CNN | 0.254 | 0.210 | 0.395 | 0.476 | 0.334 |
| RetinaNet | 0.354 | 0.210 | 0.385 | 0.471 | 0.355 |
| SSD | 0.296 | 0.199 | 0.396 | 0.470 | 0.340 |
| YOLOv3 | 0.240 | 0.139 | 0.375 | 0.472 | 0.306 |
| This application | 0.397 | 0.260 | 0.528 | 0.591 | 0.444 |

It should be understood that, although each step of the flowcharts in FIG. 2 and FIG. 6 is displayed sequentially according to arrows, the steps are not necessarily performed according to an order indicated by arrows. Unless clearly specified in this specification, there is no strict sequence limitation on the execution of the steps, and the steps may be performed in another sequence. In addition, at least some steps in FIG. 2 and FIG. 6 may include a plurality of steps or a plurality of stages. The steps or the stages are not necessarily performed at the same moment, and instead may be performed at different moments. A performing sequence of the steps or the stages is not necessarily performed in sequence, and instead may be performed in turn or alternately with another step or at least some of steps or stages of another step.

Figure 9:
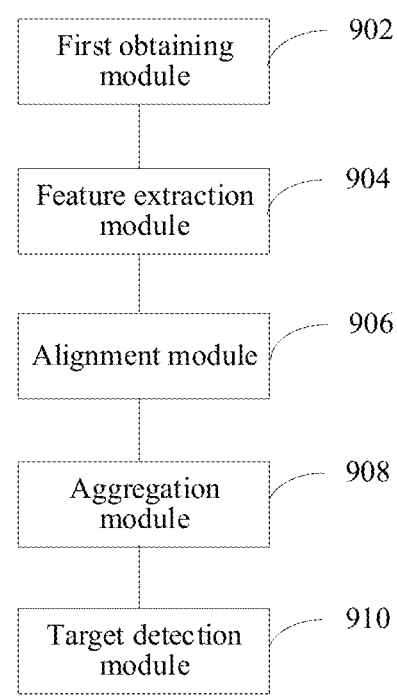
FIG. 9 is a structural block diagram of an image data detection apparatus according to an embodiment.

In an embodiment, as shown in FIG. 9, an image data detection apparatus is provided. The apparatus may be a software module or a hardware module, or a combination thereof as part of a computer device. The apparatus specifically includes a first obtaining module 902, a feature extraction module 904, an alignment module 906, an aggregation module 908, and a target detection module 910.

The first obtaining module 902 is configured to: obtain an image to be inspected, the image to be inspected including a sequence of slice images; and determine a corresponding group of slice images for each target image in the sequence of slice images, the group of slice images including the target image and an adjacent image having a context relationship with the target image in the sequence of slice images.

The feature extraction module 904 is configured to extract a corresponding slice feature map for each slice image in the group of slice images.

The alignment module 906 is configured to align operation on the slice feature maps extracted corresponding to the group of slice images.

The aggregation module 908 is configured to aggregate context information of each slice image in the group of slice images by using an aligned feature map.

The target detection module 910 is configured to: perform target region inspection on an aggregated feature map, to obtain an inspection result corresponding to the target image, and combine the inspection result corresponding to the each target image, to generate an inspection result corresponding to the image to be inspected.

In an embodiment, the alignment module 906 is further configured to: stitch the slice feature maps extracted corresponding to the group of slice images, and perform the alignment operation by using a stitched feature map, to generate the aligned feature map.

In an embodiment, the alignment module 906 is further configured to: obtain a slice quantity corresponding to the group of slice images; stack the slice feature maps extracted corresponding to the group of slice images, a stacked feature map including a slice quantity dimension and a channel dimension; and exchange a feature of the slice quantity dimension with a feature of the channel dimension, to generate the stitched feature map.

In an embodiment, the alignment module 906 is further configured to perform a three-dimensional convolution operation on the stitched feature map; normalize the slice quantity dimension and the slice size dimension of the feature map after the convolution operation; and output the aligned feature map by performing nonlinear activation on the normalized feature map.

In an embodiment, the aggregation module 908 is further configured to reshape the aligned feature map according to a slice quantity dimension, to generate a reshaped feature map; and weight the aligned feature map by using the reshaped feature map, and perform dimensionality reduction on the weighted feature map, to generate an aggregated feature map corresponding to the group of slice images.

In an embodiment, the aggregation module 908 is further configured to: transform the reshaped feature map, and weight the slice quantity dimension of the aligned feature map by using the transformed feature map; and obtain a dimensionality reduction convolution, and perform dimensionality reduction on the weighted feature map by using the dimensionality reduction convolution.

In an embodiment, a convolution kernel of the dimensionality reduction convolution is generated according to a slice quantity corresponding to the group of slice images.

In an embodiment, the target detection module 910 is further configured to: identify a category corresponding to a pixel falling within a target detection box in the aggregated feature map; perform regression to obtain a bounding box of the pixel; and predict a relative distance between the pixel and a center point of the target detection box, and filter out the bounding box of the pixel when the relative distance exceeds a preset distance.

Figure 10:
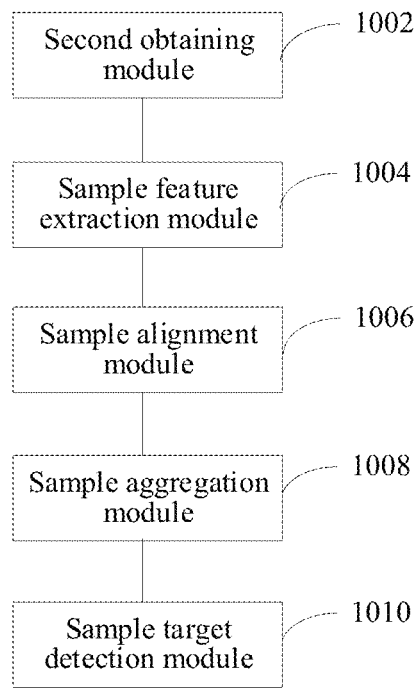
FIG. 10 is a structural block diagram of an apparatus for training an image inspection model according to an embodiment.

In an embodiment, an apparatus for training an image inspection model is provided. The image inspection model includes a backbone network, a three-dimensional alignment network, a three-dimensional aggregation network, and a target detection network. The apparatus may be a software module or a hardware module, or a combination thereof as part of a computer device. As shown in FIG. 10, the apparatus includes a second obtaining module 1002, a sample feature extraction module 1004, a sample alignment module 1006, a sample aggregation module 1008, and a sample target detection module 1010.

The second obtaining module 1002 is configured to determine a corresponding group of slice sample images for each target sample image in a sequence of slice sample images of an image sample; the group of slice sample images including the target sample image and an adjacent sample image having a context relationship with the target sample image in the sequence of slice sample images.

The sample feature extraction module 1004 is configured to extract a corresponding slice sample feature map for each slice sample image in the group of slice sample images through the backbone network.

The sample alignment module 1006 is configured to align operation on the slice sample feature maps extracted corresponding to the group of slice sample images through the three-dimensional alignment network.

The sample aggregation module 1008 is configured to aggregate context information of each slice sample image in the group of slice sample images through the three-dimensional aggregation network by using an aligned sample feature map.

The sample target detection module 1010 is configured to: perform target region inspection on an aggregated sample feature map through the target detection network, to obtain an inspection result corresponding to the target sample image, and combine the inspection result corresponding to each target sample image, to generate an inspection result corresponding to the image sample.

In an embodiment, the sample alignment module 1006 is further configured to stitch the slice sample images extracted corresponding to the group of slice sample images through the three-dimensional alignment network, and perform the alignment operation by using a stitched sample feature map, to generate the aligned sample feature map.

In an embodiment, the sample aggregation module 1008 is further configured to: reshape the aligned sample feature map according to a slice quantity dimension through the three-dimensional aggregation network, to generate a reshaped sample feature map; and weight the aligned sample feature map by using the reshaped sample feature map, and perform dimensionality reduction on the weighted sample feature map, to generate an aggregated sample feature map corresponding to the group of slice sample images.

In an embodiment, the target detection network includes a classification branch, a regression branch, and a center point prediction branch. The sample target detection module 1010 is further configured to: identify a category corresponding to a sample pixel falling within a target detection box in the aggregated sample feature map through the classification branch; perform regression through the regression branch to obtain a bounding box of the sample pixel; and predict a relative distance between the sample pixel and a center point of the target detection box through the center point prediction branch, and filter out the bounding box of the sample pixel when the relative distance exceeds a preset distance.

In an embodiment, the sample target detection module 1010 is further configured to: obtain a slice thickness, and determine a slice adjustment quantity according to the slice thickness; and perform a non-maximum suppression operation by using the slice adjustment quantity of slice sample images, to remove redundant detection boxes.

For a specific limitation on the image data detection apparatus, refer to the limitation on the image data inspection method above. For a specific limitation on the apparatus for training an image inspection model, refer to the limitation on the method for training an image inspection model above. Details are not described herein again. The modules in the foregoing image data detection apparatus and apparatus for training an image inspection model may be implemented entirely or partially by software, hardware, or a combination thereof. The foregoing modules may be built in or independent of a processor of a computer device in a hardware form, or may be stored in a memory of the computer device in a software form, so that the processor invokes and performs an operation corresponding to each of the foregoing modules.

In an embodiment, a computer device is provided. The computer device may be a server, and an internal structure diagram thereof may be shown in FIG. 11. The computer device includes a processor, a memory, and a network interface connected through a system bus. The processor of the computer device is configured to provide computing and control capabilities. The memory of the computer device includes a non-volatile storage medium and an internal memory. The non-volatile storage medium stores an operating system, computer-readable instructions, and a database. The internal memory provides an environment for running of the operating system and the computer-readable instructions in the non-volatile storage medium. The database of the computer device is configured to store image data. The network interface of the computer device is configured to communicate with an external terminal through a network connection. The computer-readable instructions are executed by the processor to implement an image data inspection method, or a method for training an image inspection model.

Figure 11:
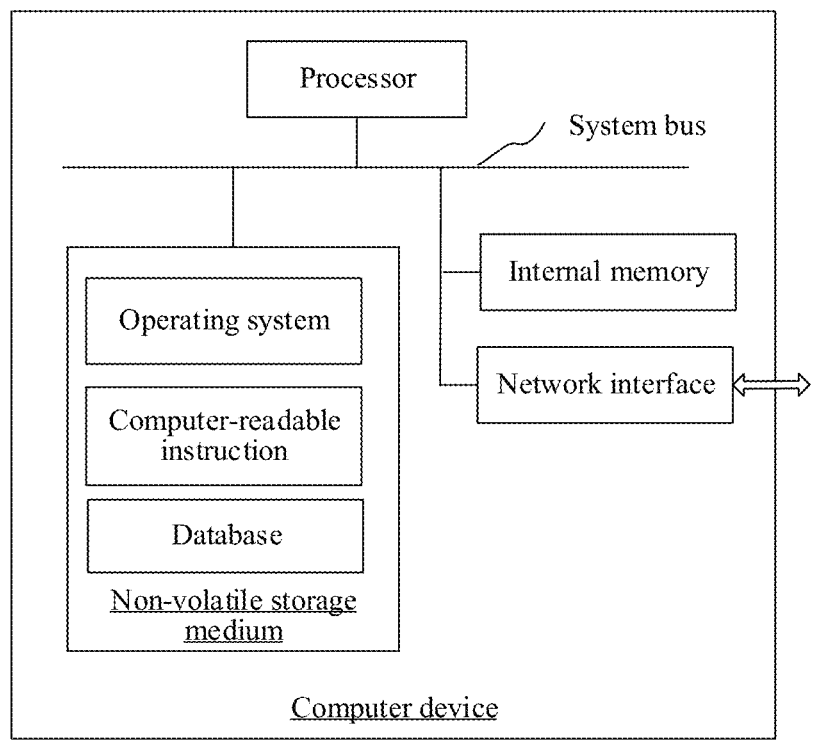
FIG. 11 is a diagram of an internal structure of a computer device according to an embodiment.

A person skilled in the art may understand that the structure shown in FIG. 11 is only a block diagram of a part of a structure correlated to a solution of this application and does not limit the computer device to which the solution of this application is applied. Specifically, the computer device may include more or fewer members than those in the drawings, or include a combination of some members, or include different member layouts.

In one embodiment, a computer device is further provided, including a memory and a processor, the memory storing computer-readable instructions, the computer-readable instructions, when executed by the processor, implementing the steps in the foregoing method embodiments.

In one embodiment, one or more non-volatile storage mediums storing computer-readable instructions are provided, the computer-readable instructions, when executed by one or more processors, causing the one or more processors to perform the steps in the foregoing method embodiments.

In one embodiment, a computer program product or a computer program is provided. The computer program product or the computer program includes computer instructions, and the computer instructions are stored in a computer-readable storage medium. The processor of the computer device reads the computer instructions from the computer-readable storage medium, and the processor executes the computer instructions, to cause the computer device to perform the steps in the method embodiments.

A person of ordinary skill in the art may understand that all or some of procedures of the method in the foregoing embodiments may be implemented by a computer program by instructing relevant hardware. The computer program may be stored in a non-volatile computer-readable storage medium. When the computer program is executed, the procedures of the foregoing method embodiments may be implemented. Any reference to a memory, a storage, a database, or another medium used in the embodiments provided in this application may include at least one of a non-volatile memory and a volatile memory. The non-volatile memory may include a read-only memory (ROM), a magnetic tape, a floppy disk, a flash memory, an optical memory, and the like. The volatile memory may include a random access memory (RAM) or an external cache. For the purpose of description instead of limitation, the RAM is available in a plurality of forms, such as a static RAM (SRAM) or a dynamic RAM (DRAM).

The technical features in the above embodiments may be combined different manners to form other embodiments. For concise description, not all possible combinations of the technical features in the embodiment are described. However, provided that combinations of the technical features do not conflict with each other, the combinations of the technical features are considered as falling within the scope recorded in this specification.

The foregoing embodiments only describe several implementations of this application, which are described specifically and in detail, but cannot be construed as a limitation to the patent scope of the present disclosure. For a person of ordinary skill in the art, several transformations and improvements can be made without departing from the idea of this application. These transformations and improvements belong to the protection scope of this application. Therefore, the protection scope of this application is subject to the protection scope of the appended claims.

What is claimed is:

1. An image data inspection method, performed by a computer, the method comprising:
   obtaining an image to be inspected, the image to be inspected comprising a sequence of slice images;
   determining a corresponding group of slice images for each target image in the sequence of slice images, the group of slice images comprising the target image and an adjacent image having a context relationship with the target image in the sequence of slice images;
   extracting a corresponding slice feature map for each slice image in the group of slice images;
   aligning the slice feature maps extracted corresponding to the group of slice images;
   aggregating context information of each slice image in the group of slice images by using an aligned feature map; and
   performing target region inspection on an aggregated feature map, to obtain an inspection result corresponding to the target image, and combining the inspection result corresponding to each target image, to generate an inspection result corresponding to the image to be inspected.

2. The method according to claim 1, wherein the aligning the slice feature maps extracted corresponding to the group of slice images comprises:
   stitching the slice feature maps extracted corresponding to the group of slice images, and aligning the slice feature maps by using a stitched feature map, to generate the aligned feature map.

3. The method according to claim 2, wherein the stitching the slice feature maps extracted corresponding to the group of slice images comprises:
   obtaining a slice quantity corresponding to the group of slice images;
   stacking the slice feature maps extracted corresponding to the group of slice images, a stacked feature map comprising a slice quantity dimension and a channel dimension; and
   exchanging a feature of the slice quantity dimension with a feature of the channel dimension, to generate the stitched feature map.

4. The method according to claim 3, wherein the stitched feature map further comprises a slice size dimension; and aligning the slice feature maps by using a stitched feature map comprises:
   performing a three-dimensional convolution operation on the stitched feature map;
   normalizing the slice quantity dimension and the slice size dimension of the feature map after the convolution operation; and
   outputting the aligned feature map by performing nonlinear activation on the normalized feature map.

5. The method according to claim 1, wherein the aggregating context information of each slice image in the group of slice images by using an aligned feature map comprises:
   reshaping the aligned feature map according to a slice quantity dimension, to generate a reshaped feature map;
   weighting the aligned feature map by using the reshaped feature map; and
   performing dimensionality reduction on the weighted feature map, to generate an aggregated feature map corresponding to the group of slice images.

6. The method according to claim 5, wherein the weighting the aligned feature map by using the reshaped feature map, and performing dimensionality reduction on the weighted feature map comprises:
   transforming the reshaped feature map, and weighting the slice quantity dimension of the aligned feature map by using the transformed feature map; and
   obtaining a dimensionality reduction convolution, and performing dimensionality reduction on the weighted feature map by using the dimensionality reduction convolution.

7. The method according to claim 6, wherein a convolution kernel of the dimensionality reduction convolution is generated according to a slice quantity corresponding to the group of slice images.

8. The method according to claim 1, wherein the performing target region inspection on an aggregated feature map comprises:
   identifying a category corresponding to a pixel falling within a target detection box in the aggregated feature map;
   performing regression to obtain a bounding box of the pixel; and
   predicting a relative distance between the pixel and a center point of the target detection box, and filtering out the bounding box of the pixel when the relative distance exceeds a preset distance.

9. The method according to claim 1, further comprising: training an image inspection model, the image inspection model comprising a backbone network, a three-dimensional alignment network, a three-dimensional aggregation network, and a target detection network, and the training comprising:
   determining a corresponding group of slice sample images for each target sample image in a sequence of slice sample images of an image sample; the group of slice sample images comprising the target sample image and an adjacent sample image having a context relationship with the target sample image in the sequence of slice sample images;
   extracting a corresponding slice sample feature map for each slice sample image in the group of slice sample images through the backbone network;
   aligning the slice sample feature maps extracted corresponding to the group of slice sample images through the three-dimensional alignment network;
   aggregating context information of each slice sample image in the group of slice sample images through the three-dimensional aggregation network by using an aligned sample feature map; and
   performing target region inspection on an aggregated sample feature map through the target detection network, to obtain an inspection result corresponding to the target sample image, and combining the inspection result corresponding to each target sample image, to generate an inspection result corresponding to the image sample.

10. The method according to claim 9, wherein aligning the slice sample feature maps extracted corresponding to the group of slice sample images through the three-dimensional alignment network comprises:
    stitching the slice sample images extracted corresponding to the group of slice sample images through the three-dimensional alignment network, and aligning the slice feature maps by using a stitched sample feature map, to generate the aligned sample feature map.

11. The method according to claim 9, wherein the aggregating context information of each slice sample image in the group of slice sample images through the three-dimensional aggregation network by using an aligned sample feature map comprises:
    reshaping the aligned sample feature map according to a slice quantity dimension through the three-dimensional aggregation network, to generate a reshaped sample feature map;
    weighting the aligned sample feature map by using the reshaped sample feature map; and
    performing dimensionality reduction on the weighted sample feature map, to generate an aggregated sample feature map corresponding to the group of slice sample images.

12. The method according to claim 9, wherein the target detection network comprises a classification branch, a regression branch, and a center point prediction branch; and the performing target region inspection on an aggregated sample feature map through the target detection network comprises:
    identifying a category corresponding to a sample pixel falling within a target detection box in the aggregated sample feature map through the classification branch;
    performing regression through the regression branch to obtain a bounding box of the sample pixel; and
    predicting a relative distance between the sample pixel and a center point of the target detection box through the center point prediction branch, and filtering out the bounding box of the sample pixel when the relative distance exceeds a preset distance.

13. The method according to claim 12, wherein the method further comprises:
    obtaining a slice thickness corresponding to the slice sample image, and determining a slice adjustment quantity according to the slice thickness; and
    performing a non-maximum suppression operation by using the slice adjustment quantity of slice sample images, to remove redundant detection boxes.

14. One or more non-transitory storage media storing computer-readable instructions, the computer-readable instructions, when executed by one or more processors, causing the one or more processors to perform:
    obtaining an image to be inspected, the image to be inspected comprising a sequence of slice images;
    determining a corresponding group of slice images for each target image in the sequence of slice images, the group of slice images comprising the target image and an adjacent image having a context relationship with the target image in the sequence of slice images;
    extracting a corresponding slice feature map for each slice image in the group of slice images;
    aligning the slice feature maps extracted corresponding to the group of slice images;

aggregating context information of each slice image in the group of slice images by using an aligned feature map; and performing target region inspection on an aggregated feature map, to obtain an inspection result corresponding to the target image, and combining the inspection result corresponding to each target image, to generate an inspection result corresponding to the image to be inspected.

15. The storage media according to claim 14, wherein the aligning the slice feature maps extracted corresponding to the group of slice images comprises:

stitching the slice feature maps extracted corresponding to the group of slice images, and aligning the slice feature maps by using a stitched feature map, to generate the aligned feature map.

16. The storage media according to claim 15, wherein the stitching the slice feature maps extracted corresponding to the group of slice images comprises:

obtaining a slice quantity corresponding to the group of slice images;

stacking the slice feature maps extracted corresponding to the group of slice images, a stacked feature map comprising a slice quantity dimension and a channel dimension; and exchanging a feature of the slice quantity dimension with a feature of the channel dimension, to generate the stitched feature map.

17. The storage media according to claim 16, wherein the stitched feature map further comprises a slice size dimension; and aligning the slice feature maps by using a stitched feature map comprises:

performing a three-dimensional convolution operation on the stitched feature map;

normalizing the slice quantity dimension and the slice size dimension of the feature map after the convolution operation; and outputting the aligned feature map by performing nonlinear activation on the normalized feature map.

18. The storage media according to claim 14, wherein the aggregating context information of each slice image in the group of slice images by using an aligned feature map comprises:

reshaping the aligned feature map according to a slice quantity dimension, to generate a reshaped feature map;

weighting the aligned feature map by using the reshaped feature map; and performing dimensionality reduction on the weighted feature map, to generate an aggregated feature map corresponding to the group of slice images.

19. The storage media according to claim 18, wherein the weighting the aligned feature map by using the reshaped feature map, and performing dimensionality reduction on the weighted feature map comprises:

transforming the reshaped feature map, and weighting the slice quantity dimension of the aligned feature map by using the transformed feature map; and obtaining a dimensionality reduction convolution, and performing dimensionality reduction on the weighted feature map by using the dimensionality reduction convolution.

20. An image data inspection apparatus, comprising a memory and a processor coupled to the memory, the processor being configured to perform:

obtaining an image to be inspected, the image to be inspected comprising a sequence of slice images;

determining a corresponding group of slice images for each target image in the sequence of slice images, the group of slice images comprising the target image and an adjacent image having a context relationship with the target image in the sequence of slice images;

extracting a corresponding slice feature map for each slice image in the group of slice images;

aligning the slice feature maps extracted corresponding to the group of slice images;

aggregating context information of each slice image in the group of slice images by using an aligned feature map; and performing target region inspection on an aggregated feature map, to obtain an inspection result corresponding to the target image, and combining the inspection result corresponding to each target image, to generate an inspection result corresponding to the image to be inspected.

* * * * *